United States Patent [19]

Böger et al.

[11] 4,246,283
[45] Jan. 20, 1981

[54] PESTICIDALLY ACTIVE 1-PHENYL-1,3,5-TRIAZA-4-SULFA-5-ALKYL-SULFONYL AND -PHENYLSULFONYL-PENT-1-EN DERIVATIVES

[75] Inventors: Manfred Böger, Weil am Rhein, Fed. Rep. of Germany; Jozef Drabek, Allschwil, Switzerland

[73] Assignee: Ciba-Geigy Corporation, Ardsley, N.Y.

[21] Appl. No.: 802,226

[22] Filed: Jun. 1, 1977

[30] Foreign Application Priority Data

Jun. 4, 1976 [CH] Switzerland .......................... 7112/76
Feb. 9, 1977 [CH] Switzerland .......................... 1560/77
May 13, 1977 [CH] Switzerland .......................... 6014/77

[51] Int. Cl.³ ................. C07C 143/75; C07C 143/79; A01N 9/16
[52] U.S. Cl. ..................... 424/321; 564/91; 564/97; 564/99
[58] Field of Search ................. 424/321; 260/556 A, 260/556 AR, 551 S

[56] References Cited

U.S. PATENT DOCUMENTS

| 3,285,929 | 11/1966 | Klauke et al. .......... 260/551 S |
| 3,703,500 | 11/1972 | Nast et al. .......... 260/556 A |
| 3,939,192 | 2/1976 | Kühle et al. .......... 424/298 X |
| 3,947,591 | 3/1976 | Rizzo et al. .......... 260/551 S X |
| 3,954,836 | 5/1976 | Siegle et al. .......... 260/551 S X |
| 3,998,969 | 12/1976 | Rizzo .......... 424/324 |
| 4,017,638 | 4/1977 | Dittrich et al. .......... 424/321 |
| 4,056,570 | 11/1977 | Pallos .......... 260/556 AR X |
| 4,140,795 | 2/1979 | Böger et al. .......... 260/556 A X |

FOREIGN PATENT DOCUMENTS 867985 12/1978 Belgium .

OTHER PUBLICATIONS

Wilson et al., Textbook of Org. Med. & Pharm. Chem., 5th Ed., Lippincott Co., pp. 38–40 (1966).

*Primary Examiner*—Thomas A. Waltz
*Attorney, Agent, or Firm*—Frederick H. Rabin; John J. Maitner

[57] ABSTRACT

Compounds of the formula

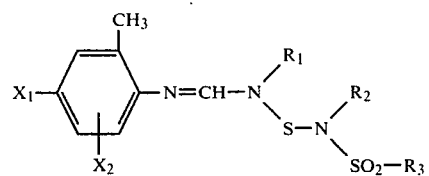

wherein $R_1$ is methyl or ethyl, $R_2$ is $C_1$–$C_{12}$-alkyl, $C_3$–$C_6$-cycloalkyl or cyclopropylmethyl, $R_3$ is $C_1$–$C_4$-alkyl or phenyl optionally mono-, or di- or trisubstituted by halogen and/or methyl and either (i) $X_1$ is methyl, chlorine, bromine or hydrogen and $X_2$ is methyl or (ii) $X_1$ is methyl, chlorine or bromine and $X_2$ is hydrogen exhibit valuable pesticidal, in particular acaricidal and insecticidal, properties.

18 Claims, No Drawings

PESTICIDALLY ACTIVE 1-PHENYL-1,3,5-TRIAZA-4-SULFA-5-ALKYLSULFONYL AND -PHENYLSULFONYL-PENT-1-EN DERIVATIVES

The present invention relates to novel 1-phenyl-1,3,5-triaza-4-sulpha-5-alkylsulphonyl- and -5-phenylsulphonylpent-1-ene derivatives which act against pests, a process for their manufacture, and to pesticidal compositions which contain these derivatives as active ingredient, and to a method of controlling pests which comprises the use of the novel derivatives.

The 1-phenyl-1,3,5-triaza-4-sulpha-5-alkylsulphonyl- and -5-phenylsulphonyl-pent-1-ene derivatives have the formula I

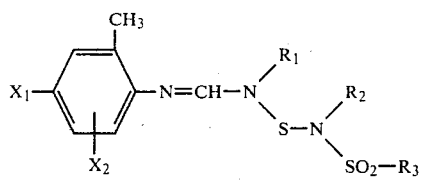

wherein
$R_1$ represents a methyl or ethyl group,
$R_2$ represents a $C_1$–$C_{12}$-alkyl, $C_3$–$C_6$-cycloalkyl or cyclopropylmethyl group,
$R_3$ represents a $C_1$–$C_4$-alkyl group or a phenyl group optionally mono-, di- or tri-substituted by one or more halogen atoms and/or methyl groups,
and either (i)

$X_1$ represents a methyl group or a chlorine, bromine or hydrogen atom and
$X_2$ represents a methyl group, or (ii)

$X_1$ represents a methyl group or a chlorine or bromine atom and
$X_2$ represents a hydrogen atom.

Alkyl groups $R_2$ and $R_3$ can be branched or straight-chain. Suitable examples of such groups are the methyl, ethyl, n-propyl, isopropyl and n-, iso-, sec.- and tert.-butyl group as well as, for $R_2$, the n-pentyl, n-hexyl, n-octyl, n-decyl and n-dodecyl group and the isomers thereof. The term "cycloalkyl group" is to be understood as meaning the cyclopropyl, cyclopentyl and cyclohexyl group.

Particularly preferred compounds on account of their action against pests, especially against insects and chiefly against representatives of the order Acarina, are those of the formula I wherein
$R_1$ represents a methyl group,
$X_1$ represents a methyl group or a chlorine or bromine atom, and
$X_2$ represents a hydrogen atom,
and/or those wherein
$R_2$ represents a $C_1$–$C_4$-alkyl, cyclopropyl, cyclohexyl or cyclopropylmethyl group, and
$R_3$ represents a $C_1$–$C_4$-alkyl, phenyl, monomethylphenyl, (in particular 4-methylphenyl) or monohalophenyl (in particular 4-chlorophenyl) group.

The compounds of the formula I are obtained by methods which are known per se, for example by reacting a formamidine of the formula II

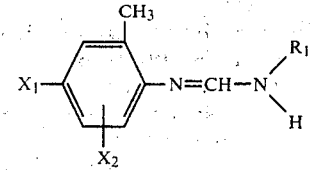

wherein $R_1$, $X_1$ and $X_2$ have the meanings given above, in the presence of a base, with a compound of the formula III

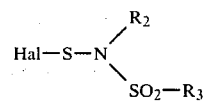

wherein $R_2$ and $R_3$ have the meanings given above and "Hal" represents a halogen atom, in particular a chlorine or bromine atom.

The process is carried out at a reaction temperature between $-20°$ and $+30°$ C., at normal or elevated pressure, and preferably in a solvent or diluent which is inert to the reactants or in an excess of the base employed.

Solvents and diluents which are suitable for these reactions are for example: ethers and ethereal compounds, such as diethyl ether, dipropyl ether, dioxan, dimethoxyethane and tetrahydrofurane; amides, such as N,N-dialkylated carboxamides; aliphatic, aromatic and halogenated hydrocarbons, in particular benzene, toluene, xylenes, chloroform and chlorobenzene; nitriles, such as acetonitrile; dimethyl sulphoxide; and ketones, such as acetone and methyl ethyl ketone.

Suitable bases are tertiary amines, such as triethylamine, dimethyl aniline, pyridine, picolines and lutidines, and hydroxides, oxides, carbonates and bicarbonates of alkali metals and alkaline earth metals, for example potassium tert.butylate and sodium methylate.

The derivatives of the formula II and III used as starting materials are known (e.g. German Pat. specification No. 1,156,403) or they can be prepared in accordance with known methods.

The compounds of the formula I have a board biocidal action and can be used for controlling a variety of pests which are injurious to animals and plants, for example as acaricides, insecticides and ectoparasiticides.

They are suitable chiefly for controlling acarids, for example ticks and mites of the families Ixodidae, Argasidae, Tetranychidae and Dermanysidae, and, above all, for controlling ectoparasites of these families. Accordingly, the compounds of the formula I are suitable for treating crops of useful plants and primarily for external application to productive livestock or the locus of such livestock.

In addition, the compounds of the formula I have good action against a variety of insects which are injurious to plants and animals and can be used, for example, for controlling paddy stem borers (e.g. of the species *Chilo suppressalis*).

The insecticidal or acaricidal action can be substantially broadened and adapted to prevailing circumstances by the addition of other insecticides and/or acaricides. Examples of suitable additives are: organic phosphorus compounds, nitrophenols and derivatives thereof, formamidines, ureas, pyethroids, carbamates, and chlorinated hydrocarbons.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsifiable concentrates, granules, dispersions, sprays, to solutions, or suspensions, in the conventional formulation which is commonly employed in application technology. Cattle dips and spray races, in which aqueous preparations are used, are also to be mentioned.

The compositions of the present invention are manufactured in known manner by homogeneously mixing and/or grinding active substances of the formula I with the suitable carriers, with or without the addition of dispersants or solvents which are inert to the active substances.

The active substances may be processed to the following formulations:
Solid formulations:
  Dusts, tracking agents and granules (coated granules, impregnated granules and homogeneous granules).
Liquid formulations:
  (a) active substances which are dispersible in water: wettable powders, pastes and emulsions;
  (b) solutions.

The content of active substance in the above described compositions is between 0.1% and 95%, but it must be mentioned that higher concentrations can also be used if the compositions are applied from an aircraft or other appropriate application devices.

The active substances of the formula I can, for example, for formulated as follows (throughout the present specification all parts and percentages are by weight):

Dusts

The following substances are used to manufacture (a) a 5% and (b) a 2% dust:

(a)

5 parts of active substance,
95 parts of talc;

(b)

2 parts of active substance,
1 part of highly disperse silicic acid,
97 parts of talc.

The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable powder:

The following constituents are used for the preparation of (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid.

(b)

25 parts of active substance,
4.5 parts of calcium lignin sulphonate,
1.9 parts of Champagene chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin, (c)

25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin, (d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are homogeneously mixed, in suitable mixers, with the additives, the mixture being then ground in the appropriate mills and rollers. Wettable powders are obtained which can be diluted with water to give suspensions of the desired concentration.

Emulsifiable concentrates:

The following substances are used to produce (a) a 10%, (b) a 25%, and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethyl formamide,
43.2 parts of xylene;

(b)

25 parts of active substance,
2.5 parts of epoxidised vegetable oil,
10 parts of alkylarylsulphonate/fatty alcohol polyglycol ether mixture, 5 parts of dimethyl formamide,
57.5 parts of xylene;

(c)

50 parts of active substance,
4.2 parts of tributylphenol-polyglycol ether,
5.8 parts of calcium-dodecylbenzenesulphonate,
20 parts of cyclohexanone,
20 parts of xylene.

By diluting these concentrates with water it is possible to obtain emulsions of the required concentration.

Spray:

The following ingredients are used to prepare (a) a 5% spray, and (b) a 95% spray:

(a)

5 parts of active substance,
1 part of epichlorohydrin,
94 parts of ligroin (boiling range 160°–190° C.);

(b)

95 parts of active substance,
5 parts of epichlorohydrin.

The invention is further illustrated by the following Examples.

EXAMPLE 1

Preparation of 1-(2-methyl-4-chlorophenyl)-3-methyl-1,3,5-triaza-4-sulpha-5-(4-methylphenylsulphonyl)-hex-1-ene (compound 1)

A solution of N-chlorothio-N-methyl-4-toluenesulphonamide in 50 ml of methylene chloride is added with constant stirring and cooling to 0° C. to a solution of 15.5 g of N-methyl-N'-(4-chloro-2-methylphenyl)-formamidine and 8.6 g of triethylamine in 100 ml of methylene chloride.

The reaction mixture is subsequently stirred for a further ½ hour without cooling and then diluted with 100 ml of water. The methylene chloride solution is dried and then concentrated in a high vacuum, giving the compound of the formula

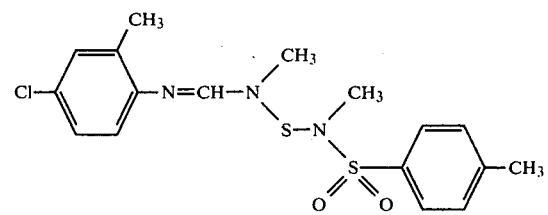

as a yellow oil with a refractive index of $n_D^{20}=1.6056$.

The following compounds of the formula I were obtained in analogous manner:

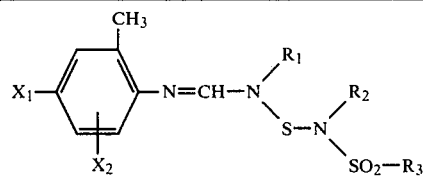

| Compound | X₁ | X₂ | R₁ | R₂ | R₃ | Physical data |
|---|---|---|---|---|---|---|
| 2 | Cl | H | CH₃ | CH₃ | CH₃ | m.p. 80°–81° C. |
| 3 | Cl | H | CH₃ | CH₃ | 4-Cl-phenyl | $n_D^{20}$: 1.6132 |
| 4 | Cl | H | CH₃ |  | CH₃ | m.p. 113°–114° C. |
| 5 | Cl | H | CH₃ | CH₃ | (n)C₄H₉ | $n_D^{20}$: 1.5699 |
| 6 | Cl | H | CH₃ | (n)C₄H₉ | CH₃ | m.p. 56°–58° C. |
| 7 | Cl | H | CH₃ | (n)C₁₂H₂₅ | CH₃ | wax |
| 8 | Cl | H | CH₃ | —CH₂—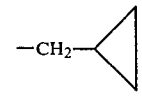 | 4-CH₃-phenyl | $n_D^{20}$: 1.5951 |
| 9 | Cl | H | CH₃ | CH₃ | phenyl | wax |
| 10 | CH₃ | H | CH₃ | CH₃ | CH₃ | m.p. 57°–59° C. |
| 11 | CH₃ | H | CH₃ | CH₃ | 4-CH₃-phenyl | $n_D^{20}$: 1.5948 |
| 12 | CH₃ | H | CH₃ |  | CH₃ | m.p. 83°–85° C. |
| 13 | CH₃ | H | CH₃ | CH₃ | (n)C₄H₉ | $n_D^{20}$: 1.5568 |
| 14 | CH₃ | H | CH₃ | (n)C₄H₉ | CH₃ | m.p. 61°–62° C. |
| 15 | CH₃ | H | CH₃ | 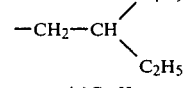 | CH₃ | $n_D^{20}$: 1.5378 |
| 16 | CH₃ | H | CH₃ | (n)C₁₂H₂₅ | CH₃ | m.p. 44°–45° C. |

-continued

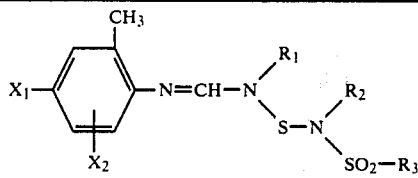

| Compound | X₁ | X₂ | R₁ | R₂ | R₃ | Physical data |
|---|---|---|---|---|---|---|
| 17 | CH₃ | H | CH₃ | —CH₂—△ | 4-CH₃-phenyl | $n_D^{20}$: 1.5869 |
| 18 | CH₃ | H | CH₃ | —⟨H⟩(cyclohexyl) | CH₃ | m.p. 102°–106° C. |
| 19 | Br | H | CH₃ | CH₃ | 4-CH₃-phenyl | $n_D^{20}$: 1.6146 |
| 20 | Cl | H | C₂H₅ | CH₃ | CH₃ | m.p. 75°–77° C. |
| 21 | H | 6-CH₃ | CH₃ | CH₃ | CH₃ | m.p. 69°–72° C. |
| 22 | Br | H | CH₃ | CH₃ | CH₃ | m.p. 82°–84° C. |
| 23 | CH₃ | 6-CH₃ | CH₃ | CH₃ | CH₃ | m.p. 97°–100° C. |
| 24 | Cl | 5-CH₃ | CH₃ | CH₃ | CH₃ | m.p. 82°–84° C. |

EXAMPLE 2

Insecticidal action: *Chilo suppressalis*

Rice seedlings of the variety Caloro were reared in plastic pots (6 seedlings per pot) so that their roots became matted to a disc. The roots were then immersed in a solution containing 800 ppm of the compound to be tested and allowed to drip off. Then each pot was populated with 5 *Chilo suppressalis* larvae in the L₂-stage and the treated plants were subsequently replaced in the pots on top of the larvae.

Percentage evaluation of mortality was made after 5 days.

The compounds of Example 1 exhibited a positive action in this test against *Chilo suppressalis.*

EXAMPLE 3

Action against ticks (I): Rhipicephalus bursa

Ten adults or approx. 100 larvae of the species *Rhipicephalus bursa* were counted into each of a number of test tubes and immersed for 1 to 2 minutes in 2 ml of an aqueous emulsion containing 100, 10, 1 or 0.1 ppm of test substance. Each test tube was then sealed with a cotton wool plug and placed on its head to enable the cotton wool to absorb excess active substance emulsion.

The mortality rate of the adults was evaluated after 2 weeks and that of the larvae after 2 days. Each test was repeated twice (development stage/active substance concentration).

In these tests, the compounds of Example 1 acted against adults and larvae of *Rhipicephalus bursa*.

EXAMPLE 4

Action against ticks (II): *Boophilus microplus* (OP-sensitive and OP-tolerant)

The test method described in Example 3 was repeated using (a) approx. 100 OP-tolerant larvae or
(b) approx. 400 OP-sensitive larvae of the species *Boophilus microplus (the tolerance refers to the tolerance to diazinone) instead of ticks of the species Rhipicephalus bursa.*

In this test, the compounds of Example 1 exhibited a good action against OP-sensitive and OP-tolerant larvae of the species *Boophilus microplus.*

EXAMPLE 5

Acaricidal action (I): *Tetranychus urticae* (OP-sensitive) and *Tetranychus cinnabarious* (OP-tolerant)

The primary larvae of Phaseolus vulgaris plants were infected 16 hours before commencement of the test with an infested piece of leaf from a mass culture of the test species. The treated plants infested with the mobile stages which had migrated to the plants were sprayed dripping wet with a test solution containing 400 ppm of the compound to be tested. Evaluation of the percentage mortality of adults and larvae (all mobile stages) was made after 24 hours and again after 7 days.

| As test species were used | the tolerance refers to the tolerance to diazinone |
|---|---|
| (a) *Tetranychus urticae* (OP-sensitive) and (b) *Tetranychus cinnabarinus* (OP-tolerant) | |

One plant was used for each test substance and test species. During the test run, the plants stood in greenhouse compartments at 25° C.

In the above test, the compounds of Example 1 exhibited a good action against both test species.

EXAMPLE 6

Acaricidal action (II): *Tetranychus urticae* (larvae/OP-tolerant)

Female (♀ ♀) adults of the species *Tetranychus urticae* (OP-tolerant) were transferred to *Phaseolus vulgaris* plants in the two-leaf stage and left thereon for 24 hours for oviposition. The adults were then removed and the larvae which had hatched from the eggs were sprayed after a further 24 hours with a test solution containing 100 ppm of the compound to be tested. Percentage evaluation of mortality was made after a further 5 days. The tolerance refers to the tolerance to diazinone. In this test, the compounds of Example 1 exhibited a good active against OP-tolerant larvae of the species *Tetranychus urticae*.

EXAMPLE 7

Acaricidal action (III): *Tetranychus urticae* (eggs/OP-tolerant)

The test for ovicidal action was carried out analogously to the larvicidal test described in Example 6, except that the test solution was sprayed onto the 24 hour-old eggs and the percentage mortality was determined 6 days later (percentage of unhatched eggs).

In this test, the compounds of Example 1 exhibited a positive ovicidal action.

What is claimed is:

1. A compound of the formula I

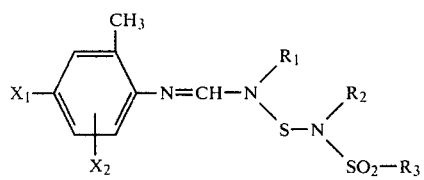

wherein
$R_1$ is methyl or ethyl,
$R_2$ is $C_1$–$C_{12}$-alkyl, $C_3$–$C_6$-cycloalkyl or cyclopropylmethyl,
$R_3$ is phenyl optionally mono-, di- or tri-substituted by halogen or methyl, and either
(i)
   $X_1$ is methyl, chlorine, bromine or hydrogen and
   $X_2$ is methyl, or
(ii)
   $X_1$ is methyl, chlorine or bromine and
   $X_2$ is hydrogen.

2. A compound according to claim 1 wherein
$R_1$ is methyl,
$X_1$ is methyl, chlorine or bromine and
$X_2$ is hydrogen.

3. A compound according to claim 2 wherein
$R_2$ is $C_1$–$C_4$-alkyl, cyclopropyl, cyclohexyl or cyclopropylmethyl and
$R_3$ is phenyl, mono-methylphenyl or mono-halophenyl.

4. A compound according to claim 3 wherein
$R_3$ is phenyl, 4-methylphenyl or 4-chlorophenyl.

5. 1-(2-Methyl-4-chlorophenyl)-3-methyl-1,3,5-triaza-4-sulfa-5-(4-methylphenylsulfonyl)-hex-1-en according to claim 4.

6. 1-(2-Methyl-4-chlorophenyl)-3-methyl-1,3,5-triaza-4-sulfa-5-(4-chlorophenylsulfonyl)-hex-1-en according to claim 4.

7. 1-(2-Methyl-4-chlorophenyl)-3-methyl-1,3,5-triaza-4-sulfa-5-(4-methylphenylsulfonyl)-6-cyclopropyl-hex-1-en according to claim 4.

8. 1-(2-Methyl-4-chlorophenyl)-3-methyl-1,3,5-triaza-4-sulfa-5-phenylsulfonyl-hex-1-en according to claim 4.

9. 1-(2,4-Dimethylphenyl)-3-methyl-1,3,5-triaza-4-sulfa-5-(4-methylphenylsulfonyl)-hex-1-en according to claim 4.

10. 1-(2-Methyl-4-bromophenyl)-3-methyl-1,3,5-triaza-4-sulfa-5-(4-methylphenylsulfonyl)-hex-1-en according to claim 4.

11. An insecticidal or acaricidal composition comprising an insecticidally or acaricidally effective amount of a compound as defined in claim 1 together with an appropriate solid or liquid diluent therefor.

12. A composition according to claim 11 in the form of a dust, wettable powder, paste, emulsion, emulsifiable concentrate or granulate.

13. A method of controlling insects or acarid pests at a locus which method comprises applying to said locus an insecticidally or acaricidally effective amount of a compound as claimed in claim 1.

14. A method according to claim 13 wherein the locus comprises agricultural or horticultural crops.

15. A method according to claim 14 wherein the crops comprise rice cultures and the pests are insect pests.

16. A method according to claim 14 wherein the pests are acarid pests.

17. A method according to claim 13 wherein the locus comprises productive livestock or the locus of said livestock.

18. A method according to claim 13 wherein, in the compound
$X_1$ is methyl, chlorine or bromine,
$X_2$ is hydrogen,
$R_1$ is methyl,
$R_2$ is $C_1$–$C_4$-alkyl, cyclopropyl, cyclohexyl or cyclopropylmethyl and
$R_3$ is phenyl, mono-methylphenyl or mono-halophenyl.

* * * * *